United States Patent [19]
Friedheim

[11] 3,974,148
[45] Aug. 10, 1976

[54] FILARICIDAL AND TRYPANOCIDAL PHENYLARSENODITHIO COMPOUNDS

[76] Inventor: Ernst A. H. Friedheim, 5, Avenue Marc Monnier, Geneva, Switzerland

[22] Filed: July 11, 1972

[21] Appl. No.: 270,820

[30] Foreign Application Priority Data
July 20, 1971 Switzerland................. 10701/71

[52] U.S. Cl................. 260/242; 424/245
[51] Int. Cl.$^2$............................ C07F 9/80
[58] Field of Search............ 260/440, 242

[56] References Cited
UNITED STATES PATENTS

| | | | |
|---|---|---|---|
| 1,677,392 | 7/1928 | Kharasch | 260/440 |
| 2,422,724 | 6/1947 | Friedheim | 260/242 |
| 3,466,312 | 9/1969 | Ercoli | 260/440 |

OTHER PUBLICATIONS
Banks et al., J. Am. Chem. Soc., vol. 66, pp. 1771–1775 (1944).

Primary Examiner—Harry I. Moatz
Attorney, Agent, or Firm—Stevens, Davis, Miller & Mosher

[57] ABSTRACT

Filaricidal and trypanocidal phenylarsenodithio compounds of the formula

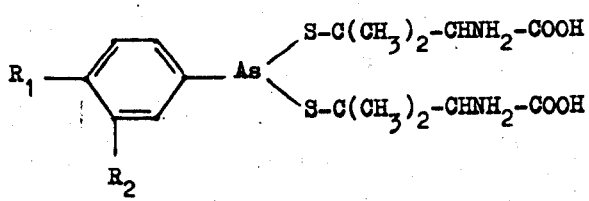

I wherein $R_1$ is —OH or —CO.NH$_2$ or the rest

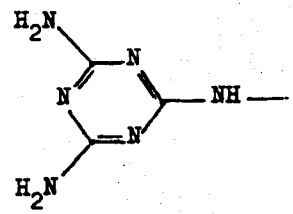

and $R_2$ is hydrogen or the amino group, as well as salts of these compounds with acids and bases.

2 Claims, No Drawings

FILARICIDAL AND TRYPANOCIDAL PHENYLARSENODITHIO COMPOUNDS

The present invention concerns filaricidal and trypanocidal phenylarsenodithio compounds of the formula

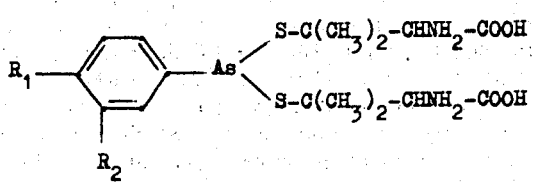

wherein $R_1$ is —OH or —CO.NH$_2$ or the radical

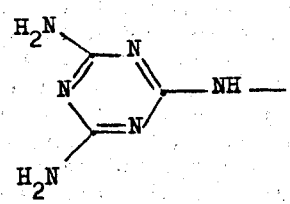

and $R_2$ is hydrogen or the amino group, as well as salts of these compounds with acids and bases.

These new compounds can be manufactured by reacting about 1 mole of a phenylarsenoxide of the formula

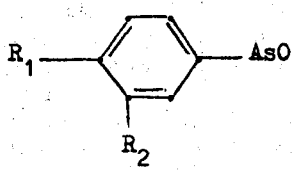

wherein $R_1$ and $R_2$ have the same meaning as above, with about 2 moles of D-penicillamine of the formula $$(CH_3)_2CSH—CHNH_2COOH$$

The starting material D-penicillamine is also known as beta,beta-dimethyl cysteine, or as beta-mercapto valine.

The new compounds of the present invention have filaricidal and trypanocidal activities. They may be applied orally or parenterally in usual pharmaceutical farriers. The new compounds are stable, so that their solutions and suspensions may be sterilized at temperatures up to 100°C.

The new compounds can be used for the treatment of diseases caused by parasites, in particular of diseases of man and animals caused by trypanosomes and filaria.

The parasites causing the diseases known as "filariasis" exist in man and in some animals, e.g. in cats and dogs, in two forms: the adult worms, also called "macrofilaria", and embryonic forms known as "microfilaria", representing the offspring of the macrofilaria. A parasitological treatment demands the extermination within the host of both forms. Current therapy of filariasis is based on the drug diethylcarbamazine, which in well tolerated single and triple doses is active on the microfilaria, but has little or no effect on the macrofilaria.

The new therapeutical effect of the new compounds according to the invention is a lethal effect of a single dose on the macrofilaria, demonstrated in the cotton rat infected with Litmosoides Carinii and in man infected with Wucheria Bancrofti. After the adult worms i.e. the macrofilaria have been killed, the microfilaria disappear slowly, but definitly, as they reach the end of their natural lifespan. Thus, the new compounds allow a causal therapy and cure of human bancroftian filariasis with a single well tolerated dose.

Preferably, the following compounds are used:

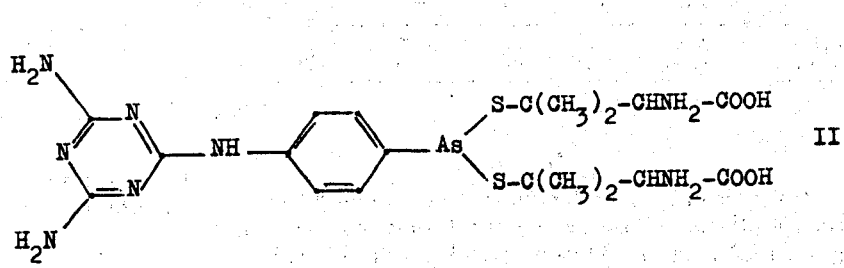

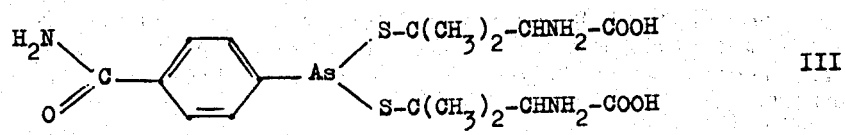

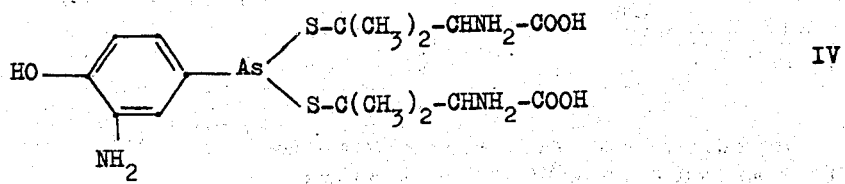

These compounds can be manufactured by reacting the corresponding phenylarsenoxide with D-penicillamine.

Preferably, the reaction is carried out in water or in a lower alcohol or in an aqueous lower alcohol. The reaction temperature is advantageously between 20° and 100°C, preferably between 40° to 80°C.

Acid addition salts of the new compounds can be obtained directly by conducting the reaction at a pH from 1-4 by addition of hydrochloric, sulfuric, phosphoric, methanesulfonic or other inorganic or organic acids, such as citric acid or tartaric acid.

Salts with bases can be obtained by dissolving the reaction products in water or lower alcohols by addition of bases to a pH of 9-10 and — if desired — followed by precipitation of the salts with organic liquids. For such precipitation ethanol, isopropanol, isopropylether, aceton or chloroform may be used. Suitable bases include anorganic bases such as sodium hydroxide, or potassium hydroxide, organic bases such as diethylamine, 1,6-diaminohexane, methylgluconate.

EXAMPLE 1

A solution of 50 g p-melaminylphenylarsenoxide in 500 ml methanol of 50°C is introduced in to a solution of 55 g D-penicillamine in 1000 ml methanol of 50°C. The resulting clear solution is stirred for 30 minutes at 70°-80°C. A white precipitate is formed and filtered off, after cooling of the reaction mixture, washed with cold water and ethanol and dried in vacuum. The yield is 92 g. The product corresponds to formula II. It is a white powder, insoluble in water, methanol, ethanol, acetone; soluble in aquous acids such as hyddrochloric, sulfuric, phosphoric tartaric, citric, acetic acid, and in aquous alcali such as sodium carbonate, potassium hydroxide, ammonia, diethylamine, 1,6-diaminohexane, methylglucamine.

|  | C% | H% | N% | S% | As% |
|---|---|---|---|---|---|
| calc. | 39.4 | 5.0 | 18.8 | 11.7 | 12.6 |
| found | 39.86 | 5.11 | 19.57 | 11.20 | 13.08 |

EXAMPLE 2

50 g p-melaminylphenylarsenoxide are introduced in small portions, with stirring into a hot solution of 52.5 g D-penicillamine in 500 ml of water heated to 80° and 12.5 g 84–85 phosphoric acid. The resulting clear solution is filtered hot. The white precipitate which forms on cooling, is filtered off, washed with ice water and ethanol and dried in vacuum. The product is re-crystalized from hot water. Yield 60 g. The product is the phosphate of II, consisting of 1 mol of II and 1 mol of $H_3PO_4$.

|  | C% | H% | N% | S% | P% | As% |
|---|---|---|---|---|---|---|
| calc. | 33.7 | 5.0 | 16.2 | 9.60 | 4.7 | 11.4 |
| found | 34.0 | 4.8 | 16.7 | 9.55 | 4.6 | 11.2 |

The product is a white powder, soluble in hot water, in aquous alkali such as KOH, ammonia, diethylamine, 1,6-diaminohexane; insoluble in ethanol, ether, chloroform.

If in the preceding example phosphoric acid is replaced by sulfuric acid, methanesulfonic acid or citric acid, the corresponding sulfate, methansulfonate citrate is formed.

EXAMPLE 3

20.0 g of the product prepared according to example 1 of formula II are dissolved in 40 ml of methanol and 10 ml of diethylamine. The resulting clear solution is mixed, under stirring, with 80 ml of isopropylether. After standing for 12 hours at 8°C the resulting white precipitate is separated by decantation, washed repeatedly with isopropylether and dried in vacuum. The yield is 15.8 g of a white powder, which is soluble in water and methanol, insoluble in ether and chloroform. It is a salt of product II with diethylamine.

EXAMPLE 4

10 g of the product prepared according to example 1, corresponding to formula II are dissolved in a mixture of 150 ml of ethanol and 10 g of diaminohexane, warmed to 40°C. On addition of 150 ml of chloroform to the solution cooled to 10°C, a white resin precipitates, which is separated by decantation, washed repeatedly with chloroform and dried in vacuum. The dry resin is powdered. The yield is 11 g of a white powder, which is soluble in water and methanol, insoluble in chloroform, benzene and ether. The product is a salt of the product of formula II with 1,6-diaminohexane.

EXAMPLE 5

10 g of p-benzamidophenylarsenoxide and 15 g D-penicillamine are boiled, with refluxing, for 40 minutes, in 300 ml water. After cooling, the remaining white product is filtered off, washed with cold water and recrystallized from 300 ml of boiling water. The yield is 12 g of a white powder, soluble in hot water, sodium hydroxide and hydrochloric acid, insoluble in ethanol, acetone and chloroform.

|  | C% | H% | N% | S% | As% |
|---|---|---|---|---|---|
| calc. | 41.55 | 5.3 | 8.55 | 13.03 | 15.27 |
| found | 41.10 | 5.4 | 8.4 | 12.93 | 15.15 |

The product forms salts with acids and bases, according to examples 2,3 and 4.

EXAMPLE 6

20 g of 4-hydroxy-3-amino-phenylarsenoxide and 33 g of d-penicillamine are stirred, with refluxing, in 500 ml methanol. The reaction mixture is cooled to 10°C and the resulting white precipitate is filtered off, washed with cold methanol and dried in vacuum. The yield is 41 g of a white powder, which is soluble in hot water, dilute aquous acids and bases, insoluble in isopropylalcohol, acetone, ether and chloroform. The compound has the formula IV.

|  | C% | H% | N% | S% | As% |
|---|---|---|---|---|---|
| calc. | 40.08 | 5.43 | 8.77 | 13.36 | 15.66 |
| found | 41.2 | 5.5 | 8.70 | 13.3 | 15.3 |

The product forms salts with acids and bases, according to examples 2, 3 and 4.

The compound of formula II has been tested in the following manner:

1. Filaricidal effects of 10 × 40 mg/kg of compound II 12 cotton rats are exposed to 100–200 infected mites of L. bacoti. Some months after the infection 8 rats of the group receive one subcutaneous injection of 40 mg/kg of compound II per day for 10 consecutive days. The remaining 4 rats of the group are not treated.

All animals are killed and autopsied 1 month after the treatment. The significant data of this experiment and post mortem findings are recorded in table 1.

Table 1

| rat no | treat. 10 × 40 mg/kg | worms in pleural cavities | | | mf/5cmm blood | | months between infection and treat. |
|---|---|---|---|---|---|---|---|
| | | living | | dead | before | 30 ds | |
| | | m | f | m + f | treat. | after treat. | |
| 1 | " | 0 | 0 | ++ | 3280 | 472 | 6 |
| 2 | " | 0 | 0 | ++ | 1291 | 404 | 5½ |
| 3 | " | 0 | 0 | ++ | 46 | 50 | 3½ |
| 4 | " | 0 | 0 | ++ | 69 | 0 | 5½ |
| 5 | " | 0 | 0 | ++ | 1253 | 360 | 5½ |
| 6 | " | 0 | 0 | ++ | 114 | 67 | 4½ |
| 7 | " | 0 | 0 | ++ | 111 | 86 | 5½ |
| 8 | " | 0 | 0 | ++ | 168 | 372 | 5½ |
| 9 | — | 7 | 23 | 0 | 591 | 1350 | |
| 10 | — | 104 | 176 | 0 | 419 | 752 | |
| 11 | — | 57 | 35 | 0 | 616 | 337 | |
| 12 | — | 87 | 47 | 0 | 158 | 299 | |

Conclusion: 10 × 40 mg/kg of compound II S.C. kill the adult males and females of L.carinii in the cotton rat.

2. Prophylactic effects 12 cotton rats receive 50 mg/kg of compound II s.c. per day for 10 consecutive days. On the 5th treatment day the 12 rats under treatment and 8 untreated rats are infected by 70–149 mites of L. bacoti.

All animals are killed and autopsied 3 months after the treatment. The relevant data of the experiment and the post mortem findings are recorded in table 2.

Table 2

| rat | number of infecting mites | treatment | number of worms in pleural cavities | | | mf/5cmm blood at autopsy |
|---|---|---|---|---|---|---|
| | | | living | | dead | |
| | | | m | f | m + f | |
| 1–12 | 90, 141, 89, 100, 121, 194, 110, 126, 74, 70, 89, 92 | 10 × 50 mg/kg | 0 | 0 | 0 | 0 |
| 13 | 82 | | 20 | 59 | 0 | 524 |
| 14 | 60 | | 370 | 32 | 0 | 600 |
| 15 | 56 | | 14 | 13 | 0 | 189 |
| 16 | 77 | | 16 | 12 | 0 | 146 |
| 17 | 70 | | 6 | 5 | 0 | 24 |
| 18 | 135 | | 20 | 27 | 0 | 337 |
| 19 | 84 | | 33 | 43 | 0 | 453 |
| 20 | 149 | | 3 | 9 | 0 | 149 |

Conclusion: Full protection is afforded against an infection with L. carinii by infected mites, which is preceded and followed by 5 s.c. doses of 50 mg/kg of compound II.

The embodiments of the invention in which an exclusive property or privilege is claimed are defined as follows:

1. The phenylarsenodithio compound of formula

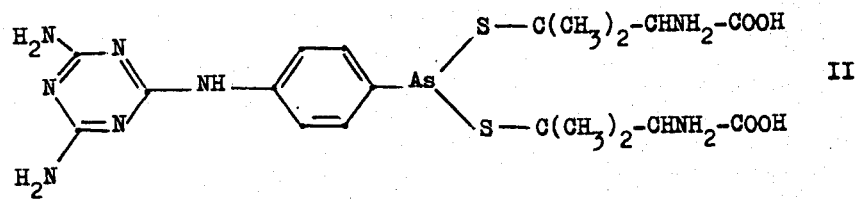

2. A salt of the compound:

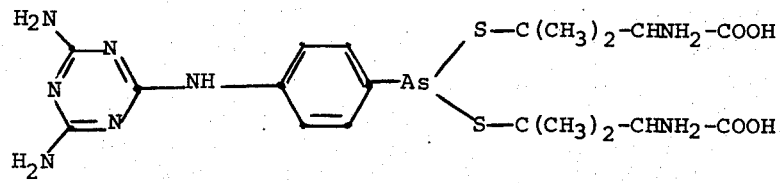

* * * * *